United States Patent [19]

Kern et al.

[11] Patent Number: 4,705,803
[45] Date of Patent: Nov. 10, 1987

[54] METHOD OF IMPROVING RESORPTION OF INJECTED ANTIBACTERIALLY ACTIVE SUBSTANCES OR COMBINATIONS

[75] Inventors: Otto Kern; Franz Wilhelm; Ernst Salamon, all of Ingelheim am Rhein, Fed. Rep. of Germany

[73] Assignee: Boehringer Ingelheim Vetmedica GmbH, Ingelheim am Rhein, Fed. Rep. of Germany

[21] Appl. No.: 825,785

[22] Filed: Feb. 3, 1986

Related U.S. Application Data

[63] Continuation of Ser. No. 471,299, Mar. 2, 1983, abandoned.

[30] Foreign Application Priority Data

Jul. 31, 1982 [JP] Japan .................................. 57-133871

[51] Int. Cl.$^4$ .................. A61K 31/335; A61K 31/135
[52] U.S. Cl. ..................................... 514/450; 514/653
[58] Field of Search ................................ 514/450, 653

[56] References Cited

PUBLICATIONS

Chemical Abstracts 77: 773u (1972).
Chemical Abstracts 83: 65377m (1975).
Chemical Abstracts 97: 115227z (1982).
The Merck Index, 9th Ed., 1976, Merck & Co., Inc., Rahway, N.J., pp. 1260 and 1261.
Chemical Abstracts 95: 73109p (1981).
Chemical Abstracts 100: 12644j (1984).

*Primary Examiner*—Jerome D. Goldberg

*Attorney, Agent, or Firm*—Weissenberger, Hammond & Littell

[57] ABSTRACT

This invention relates to a method of improving the resorption of injected antibacterially active substances or combinations. More specifically, this invention relates to a method of increasing the resorption of an antibacterially active substance or combination which does not have optimum resorbability and which is administered parenterally into tissue, which comprises administering to a host at least one benzylamine derivative of the formula

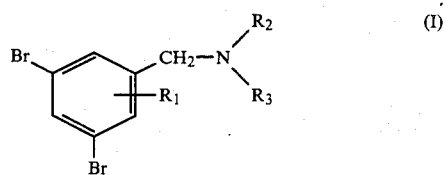

wherein
$R_1$ is a hydroxyl group in the 2- or 4-position or an amino group in the 2-position;
$R_2$ is a hydrogen atom or an alkyl group having from 1 to 3 carbon atoms; and
$R_3$ is a cyclohexyl group optionally substituted by a hydroxyl group, or a non-toxic, pharmacologically acceptable acid addition salt thereof with an inorganic or organic acid, in conjunction with said antibacterially active substance or combination.

4 Claims, No Drawings

METHOD OF IMPROVING RESORPTION OF INJECTED ANTIBACTERIALLY ACTIVE SUBSTANCES OR COMBINATIONS

This application is a continuation of co-pending U.S. patent application Ser. No. 471,299, filed Mar. 2, 1983, now abandoned.

FIELD OF THE INVENTION

This invention relates to a method of improving the resorption of injected antibacterially active substances or combinations. More specifically, this invention relates to the use of benzylamine derivatives in combination with injected antibacterially active substances or combinations to improve the resorption of said antibacterially active substances after injection.

BACKGROUND OF THE INVENTION

It is known from the literature that benzylamine derivatives are useful as bronchosecretolytics in human and veterinary medicine. The best known examples of these benzylamine derivatives are N-(2-amino-3,5-dibromobenzyl)-N-methyl-cyclohexylamine hydrochloride (generic name: bromhexine) and N-(2-amino-3,5-dibromobenzyl)-trans-4-hydroxycyclohexylamine hydrochloride (generic name: ambroxol). These compounds result in a significant increase in the quantity of secretion, but it has been found that there are a decrease in the viscosity of the secretion and a reduction in the concentration of solids in the fluid of the respiratory tract and in their specific weight, which characterize the benzylamine derivatives as secretolytics.

In addition, it is known from the literature that when the above-mentioned benzylamine derivatives are administered orally together with an antibiotic, particularly oxytetracycline and erythromycin, or with a sulfonamide such as sulfadiazine, there is an increase in the infiltration of these substances into the bronchial secretion. The same also applies to the body's own immunoglobulins, that is, immunoglobulins which have not been administered. However, this increase in the concentration of the contents of bronchial secretion is not caused by any increased resorption from the intestines induced by the above-mentioned benzylamine derivatives or by any delay in execretion through the kidneys, since there is no detectable increase in blood level values after oral or intravenous administration.

OBJECTS OF THE INVENTION

It is an object of the invention to provide a method of improving the resorption of injected antibacterially active substances or combinations.

It is also an object of this invention to provide a combination of an antibacterially active substance or combination and a benzylamine derivative.

It is a further object of this invention to provide a method of improving the resorption of an injected antibacterially active substance or combination by admixing said substance or combination with an effective amount of a benzylamine derivative of the formula

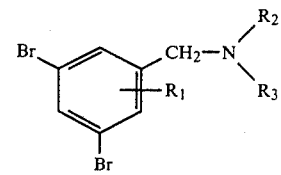

wherein
$R_1$ is a hydroxyl group in the 2- or 4-position or an amino group in the 2-position;
$R_2$ is a hydrogen atom or an alkyl group having from 1 to 3 carbon atoms; and
$R_3$ is a cyclohexyl group optionally substituted by a hydroxyl group,
or a non-toxic, pharmacologically acceptable acid addition salt thereof with an inorganic or organic acid.

These and other objects of the invention will become more apparent in the discussion below.

DETAILED DESCRIPTION OF THE INVENTION

It has now been surprisingly found that when a benzylamine derivative of the formula

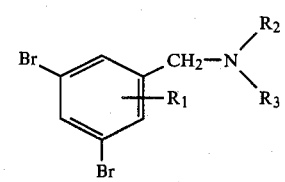

or a non-toxic, pharmacologically acceptable acid addition salt thereof with an inorganic or organic acid is administered parenterally, the resorption of an antibacterially active substance or combination which has been administered parenterally into the tissues and which, on its own, does not have optimum resorbability, is speeded up. Thus, according to the invention, as a result of the higher blood levels with the same dosage of the antibacterially active substance or combination, better and safer therapeutic results are obtained or—if higher blood levels are not wanted—the quantity administered can be reduced by comparison with the quantity required when the substance in question is administered on its own, and consequently a significant saving is achieved. Moreover, the problem of residues is solved since the injection site for the antibacterial substances and combinations in question is usually the tissue, which contains measurable residues of these substances longest.

Therefore, the present invention relates to the novel use of the benzylamine derivatives of Formula I and of the non-toxic, pharmacologically acceptable acid addition salts thereof, preferably in veterinary medicine, for increasing the resorption of antibacterially active substances or combinations which have been administered parenterally into the tissue and are not readily resorbable, preferably by parenteral administration of the benzylamine derivatives at the same time.

In Formula I,
$R_1$ is a hydroxyl group in the 2- or 4-position or an amino group in the 2-position;
$R_2$ is a hydrogen atom or an alkyl group having from 1 to 3 carbon atoms; and $R_3$ is a cyclohexyl group optionally substituted by a hydroxyl group.

The preferred benzylamine derivatives of Formula I are, however, those compounds wherein $R_2$ and $R_3$ together with the nitrogen atom between them represent an N-methyl-cyclohexylamino, N-ethyl-cyclohexylamino, trans-4-hydroxy-cyclohexylamino, or cis-3-hydroxy-cyclohexylamino group. A particularly preferred benzylamine derivative of Formula I is the compound N-(3,5-dibromo-2-hydroxybenzyl)-trans-4-hydroxycyclohexylamine or a non-toxic, pharmacologically acceptable acid addition salt thereof with an inorganic or organic acid, especially the hydrochloride salt.

Examples of antibacterial substances used according to the invention, optionally in the form of the esters or salts thereof, including the following: an antibiotic of the tetracycline group, such as oxytetracycline, oxytetracycline hydrochloride, rolitetracycline, or doxycycline; a difficultly soluble antibiotic of the β-lactam group, such as procaine penicillin, benethamine penicillin, benzathine penicillin, the benzathine salts of oxacillin, cloxacillin, or ampicillin, and of the cephalosporins; erythromycin and the derivatives thereof, such as 9-deoxy-11-deoxy-9,11-{imino-[2-(2-methoxyethoxy)-ethylidene]-oxy}-(9F)-erythromycin, erythromycin lactobionate, erythromycin ethylsuccinate, erythromycin glucoheptonate; spiramycin, spiramycin adipate; tylosin, tylosin tartrate; oleandomycin; chloramphenicol, chloramphenicol succinate; thiamphenicol, or thiamphenicol glycinate; a sulfonamide or a sodium salt thereof, such as sulfadiazine, sulfadoxine, sulfamethoxazole, sulfadimethoxine, sulfadimidine, or sulfathiazole; a sulfonamide together with an agonist such as trimethoprim, for example, the sulfdimidine/sulfathiazole/trimethoprim combination, or the sodium salts thereof; and, optionally, the delayed-release forms thereof.

The invention further relates to the new combinations which are suitable for parenteral administration into the tissue, containing a benzylamine derivative of Formula I and an antibacterial substance or combination which, on its own, does not have optimum resorbability, together with one or more conventional inert diluents or carriers, preferably those forms which are suitable for intramuscular administration. The preferred combinations are those containing (1) a benzylamine derivative of Formula I wherein $R_1$ represents a hydroxyl group and $R_2$ and $R_3$ together with the nitrogen atom between them are as defined above, but preferably represent the N-ethyl-cyclohexylamino, trans-4-hydroxycyclohexylamino, or cis-3-hydroxy-cyclohexylamino group, although especially preferably $R_1$ in the 2-position represents a hydroxyl group and $R_2$ and $R_3$ together with the nitrogen atom between them represent the trans-4-hydroxycyclohexylamino group, and (2) one of the above-mentioned antibacterial substances or combinations. A particularly preferred embodiment of the invention is directed to a combination of (1) N-(2-amino-3,5-dibromo-benzyl)-N-methyl-cyclohexylamine or a non-toxic, pharmacologically acceptable acid addition salt thereof and (2) a delayed-release oxytetracycline preparation, a delayed-release oxytetracycline hydrochloride preparation, rolitetracycline, or doxycycline;

a difficultly soluble antibiotic of the β-lactam group, such as procaine penicillin, benethamine penicillin, benzathine penicillin, a benzathine salt of oxacillin, cloxacillin, or ampicillin, and of the cephalosporins, erythromycin or a derivative thereof, such as 9-deoxy-11-deoxy-9,11-{imino-[2-(2-methoxyethoxy)-ethylidene]-oxy}-(9F)-ethromycin, erythromycin lactobionate, erythromycin ethylsuccinate, erythromycin glucoheptonate; spiramycin, spiramycin adipate; tylosin, tylosin tartrate; oleandomycin; thiamphenicol, or thiamphenicol glycinate, or a sulfonamide or a sodium salt thereof, such as sulfadiazine, sulfadoxine, sulfamethoxazole, sulfadimethoxine, sulfadimidine, or sulfathiazole, or a sulfonamide combination with an agonist such as trimethoprim, for example, the sulfadimidine/sulfathiazole/trimethoprim combination, or a combination of (1) N-(2-amino-3,5-dibromo-benzyl)-trans-4-hydroxy-cyclohexylamine or a non-toxic, pharmacologically acceptable acid addition salt thereof and (2) an antibiotic of the tetracycline group, such as oxytetracycline, oxytetracycline hydrochloride, rolitetracycline, or doxycycline, a difficultly soluble antibiotic of the β-lactam group, such as procaine penicillin, benethamine penicillin, benzathine penicillin, a benzathine salt of oxacillin, cloxacillin, or ampicillin, and of the cephalosporins, erythromycin or one of the derivatives thereof, such as 9-deoxy-11-deoxy-9,11-{imino-[2-(2-methoxyethoxy)-ethylidene]-oxy}-(9F)-erythromycin, erythromycin lactobionate, erythromycin ethylsuccinate, erythromycin glucoheptonate; spiramycin, spiramycin adipate; tylosin, tylosin tartrate; oleandomycin; chloramphenicol, chloramphenicol succinate; thiamphenicol, or thiamphenicol glycinate, or a sulfonamide or a sodium salt thereof, such as sulfadiazine, sulfadoxine, sulfamethoxazole, sulfadimethoxine, sulfadimidine, or sulfathiazole, or a combination of a sulfonamide with an agonist such as trimethoprim, for example, the sulfadimidine/sulfathiazole/trimethoprim combination, or, optionally, a corresponding delayed-release form.

The following combinations are, however, particularly preferred: (a) combinations of (1) N-(2-amino-3,5-dibromo-benzyl)-N-methyl-cyclohexylamine or a non-toxic, pharmacologically acceptable acid addition salt thereof or N-(3,5-dibromo-2-hydroxy-benzyl)-trans-4-hydroxy-cyclohexylamine or a non-toxic, pharmacologically acceptable acid addition salt thereof with (2) erythromycin, erythromycin lactobionate, erythromycin ethylsuccinate, erythromycin glucoheptonate, 9-deoxy-11-deoxy-9,11-{imino-[2-(2-methoxyethoxy)-ethylidene]oxy}-(9F)-erythromycin, tylosin, tylosin tartrate, spiramycin, spiramycin adipate, oleandomycin, benethamine penicillin, benzathine penicillin, ampicillin, oxacillin, cloxacillin, rolitetracycline, doxycycline, or a salt thereof, or a sulfonamide or a salt thereof, optionally in combination with trimethoprim, and (b) combinations of (1) N-(3,5-dibromo-2-hydroxy-benzyl)-trans-4-hydroxy-cyclohexylamine or a non-toxic, pharmacologically acceptable acid addition salt thereof with oxytetracycline or a salt thereof, chloramphenicol, chloramphenicol succinate, thiamphenicol, or thiamphenicol glycinate.

To demonstrate the efficacy of the invention, the resorption-promoting effect of the following benzylamine derivatives:

A = N-(2-amino-3,5-dibromo-benzyl)-N-methyl-cyclohexylamine hydrochloride;

B = N-(2-amino,3,5-dibromo-benzyl)-trans-4-hydroxy-cyclohexylamine hydrochloride; and C = N-(3,5-dibromo-2-hydroxy-benzyl)-trans-4-hydroxycyclohexylamine hydrochloride, was tested in the following manner:

Cattle, pigs, and sheep (with the same ten animals per group) were treated once with only the antibacterial substance or combination in question and once with the combination of the benzylamine derivative together with the same antibacterial substance or combination, administered by intramuscular route. The two treatments were given at an interval of eight days to ensure that the substance or substances administered in the first treatment had been totally eliminated. The order of treatment varied, that is, in some cases the antibacterial substance or combination (control) was administered first and in some cases the combination including the benzylamine derivative was administered first (test group). In some cases the tests were carried out as "cross-over" tests, that is, on the first occasion five animals were given the antibacterial substance or combination while five animals were given the combination including the benzylamine derivative. When the test was repeated eight days later, the treatments were reversed.

Blood samples were taken during the day at one and two hour intervals and after 24 hours, and in some cases after 32 hours as well, and in two cases (delayed-release preparations) after 48 and 72 hours also. The levels of antibiotics or sulfonamide in the blood serum were determined using conventional microbiological methods with test pathogens specific to each substance.

In each case, the areas under the blood level curves obtained were compared, as an overall measurement of antibacterial activity. This comparison showed increases in blood level for the combination of benzylamine derivatives with the antibacterial substance or combination in question, compared with the control group in question, as is shown in the following table:

TABLE 1

| Antibacterially Active Substance or Combination (Dosage: mg/kg of body weight) | Benzylamine Derivative (Dosage: mg/kg) | | Type of Animal | Increase in Blood Level (in %, compared with control) |
|---|---|---|---|---|
| Erythromycin | 10 | A 0.3 i.m. | cattle | 16.1 |
| | 10 | C 0.6 i.m. | cattle | 21.4 |
| | 10 | A 0.6 i.m. | pig | 59.1 |
| | 10 | A 1.2 i.m. | pig | 31.4 |
| Erythromycin derivative | 10 | A 1.2 i.m. | pig | 15.3 |
| | 10 | C 1.2 i.m. | pig | 45.4 |
| Oxytetracycline hydrochloride | 10 | C 0.6 i.m. | cattle | 16.3 |
| Delayed-release oxytetracycline preparation* | 20 | A 0.6 i.m. | pig | 109.5 |
| | 20 | C 1.2 i.m. | pig | 80.0 |
| Tylosin | 15 | A 0.3 i.m. | cattle | 33.0 |
| | 15 | C 0.6 i.m. | cattle | 23.5 |
| Tylosin | 10 | A 0.6 i.m. | pig | 19.3 |
| | 10 | A 1.2 i.m. | pig | 30.3 |
| | 10 | C 0.6 i.m. | pig | 30.5 |
| | 10 | C 1.2 i.m. | pig | 26.1 |
| Sulfadimidine/- | 24 | A 0.6 i.m. | pig | 29.6 |
| Sulfathiazole/- | 24 | A 1.2 i.m. | pig | 25.1 |
| Trimethoprim | 24 | C 0.6 i.m. | pig | 29.9 |
| Combination (10:10:4) | 24 | C 1.2 i.m. | pig | 20.3 |

*Blood level monitored for 72 hours; after 48 hours it is 0.13 μg/ml for the control but 0.35 μg/ml for the test group; after 72 hours, it is 0.00 μg/ml for the control but still 0.19 μg/ml for the test group.

The benzylamine derivatives of Formula I used according to the invention and the non-toxic, pharmacologically acceptable acid addition salts thereof with inorganic or organic acids are well tolerated. For example, the acute toxicity ($LD_{50}$) in the mouse is
>400 mg/kg i.p. for Compound A,
268 mg/kg i.p. for Compound B, and
>800 mg/kg i.p. for Compound C.

In view of the above-mentioned biological characteristics, the benzylamine derivatives of Formula I and the non-toxic, pharmacologically acceptable acid addition salts thereof are, as mentioned above, suitable for improving the resorption of antibacterial substances or combinations administered parenterally into the tissue and thus help to improve and guarantee the success of the therapy. The dosage is appropriately above 0.1 mg/kg, preferably between 0.2 and 2.0 mg/kg, while in solutions the upper limit is set by the solubility of the benzylamine derivative used. For example, in water Compounds A to C have the following maximum solubilities:

| Compound | Maximum Solubility |
|---|---|
| A | 0.2 to 5.0 mg/cm$^3$ |
| B | 16.6 mg/cm$^3$ |
| C | 0.1 to 1.0 mg/cm$^3$ | dependent upon the pH, in the acid range. Obviously, higher concentrations can be achieved in oily carriers, dependent upon the solubility in oil of the benzylamine derivative and also when the benzylamine derivative is suspended in suitable carriers in which it is insoluble or not sufficiently soluble.

Moreover, the benzylamine derivative is preferably administered simultaneously with a therapeutic dose of the antibacterial substance or combination which is to be used. Examples of individual doses include the following:

TABLE 2

| Active Substance | Dose |
|---|---|
| oxytetracycline | 5 to 30 mg/kg |
| rolitetracycline | 15 to 50 mg/kg |
| doxycycline | 2 to 5 mg/kg |
| erythromycin | 5 to 20 mg/kg |
| 9-deoxy-11-deoxy-9,11-{imino-[2-(2-methoxyethoxy)-ethylidene]-oxy}-(9F)-erythromycin | 5 to 20 mg/kg |
| spiramycin | 10 to 50 mg/kg |
| tylosin | 5 to 20 mg/kg |
| chloramphenicol | 10 to 50 mg/kg |
| thiamphenicol | 10 to 50 mg/kg |
| sulfadiazine | 15 to 50 mg/kg |

TABLE 2-continued

| Active Substance | Dose |
| --- | --- |
| sulfadiazine/sulfathiazole/trimethoprim | 15 to 30 mg/kg |
| sulfadoxin/trimethoprim | 15 to 30 mg/kg |
| procaine penicillin | 2000 to 20,000 I.U./kg |
| benzathine penicillin | 6000 to 25,000 I.U./kg |
| ampicillin | 2 to 15 mg/kg |
| oxacillin | 5 to 15 mg/kg |
| cloxacillin | 5 to 15 mg/kg |
| oxytetracycline hydrochloride | 2 to 25 mg/kg |

Examples of suitable forms for administration include injectable preparations of an aqueous, water-miscible or oily nature in which the antibacterial substances in question are dissolved or suspended in the desired concentration. The same also applies to the benzylamine derivatives or the salts thereof, depending on their solubility, while the same preparation may contain one substance in solution and the other in suspension. In those cases where an aqueous solution is desired but is not practicable due to insufficient stability, such as of the antibiotic, the injectable combination is prepared shortly before administration by dissolving or suspending the dry substance in the solvent containing the benzylamine derivative.

The benzylamine derivatives of Formula I and the nontoxic, pharmacologically acceptable acid addition salts thereof used according to the invention are known from the literature. See, for example, U.S. Pat. Nos. 3,336,308, 3,536,713, and 4,113,777, incorporated herein by reference.

The compounds of Formula I may be obtained in the form of their non-toxic, pharmacologically acceptable acid salts after reaction with inorganic or organic acids. Suitable acids include, for example, hydrochloric, hydrobromic, sulfuric, methylsulfuric, phosphoric, tartaric, fumaric, citric, maleic, succinic, gluconic, malic, p-toluenesulfonic, methanesulfonic, and amidosulfonic acid.

The following examples are intended to illustrate the invention and should not be construed as limiting the invention thereto.

EXAMPLES

Example 1

Two-compartment preparation containing 9-deoxy-11-deoxy-9,11-{imino-[2-(2-methoxyethoxy)-ethylidene]-oxy}-(9F)-erythromycin lactobionate and N-(2-amino-3,5-dibromo-benzyl)-N-methyl-cyclohexylamine hydrochloride (aqueous solution)

Composition:

| (a) Dry ampule. | |
| --- | --- |
| Antibiotic | 715.0 mg |
| (b) Solution ampule. | |
| Active substance | 75.0 mg |
| Tartaric acid | 37.5 mg |
| Glycerin polyethyleneglycol oxystearate | 250.0 mg |
| Glucose | 200.0 mg |
| Water for injection q.s. ad | 5.0 ml |

Method:

To prepare the dry ampule, the active substance is dissolved in water for injection, sterilized, and freed from pyrogens by means of a suitable filter system, possibly by use of pyrogen adsorption layers, and then transferred under aseptic conditions, in the desired dosages, into 10 ml injection vials which have been cleaned and sterilized. These vials are freeze-dried in the usual way.

Next, to prepare the solution ampules, the active substance and excipients are successively dissolved in water for injection purposes, filtering is carried out in the same way as with the dry ampule solution, and the resulting solution is transferred into 5 ml ampules. For sterilization, the fused ampules and the injection vials, sealed with rubber stoppers and crimped aluminium caps, are heated to 121° C. for 20 minutes.

Example 2

Two-compartment preparation containing 9-deoxy-11-deoxy-9,11-{imino-[2-(methoxyethoxy)-ethylidene]-oxy}-(9F)-erythromycin lactobionate and N-(2-amino-3,5-dibromobenzyl)-N-methylcyclohexylamine hydrochloride (aqueous solution)

Composition:

| (a) Dry ampule. | |
| --- | --- |
| Antibiotic | 3575.0 mg |
| (b) Solution ampule. | |
| Active substance | 375.0 mg |
| Tartaric acid | 187.5 mg |
| Glycerin polyethyleneglycol oxystearate | 1250.0 mg |
| Glucose | 1000.0 mg |
| Water for injection q.s. ad | 25.0 ml |

Method:

The ampules (a) and (b) are prepared by a procedure analogous to that of Example 1. However, the substance is transferred into 25 ml or 30 ml injection vials.

Example 3

Oily suspension containing 9-deoxy-11-deoxy-9,11-{imino-[2-(2-methoxyethoxy)-ethylidene]-oxy}-(9F)-erythromycin and N-(3,5-dibromo-2-hydroxy-benzyl)-trans-4-hydroxycyclohexylamine hydrochloride Composition:

| Antibiotic | 500.0 mg |
| --- | --- |
| Active substance | 100.0 mg |
| Benzyl alcohol | 50.0 mg |
| Neutral oil q.s. ad | 5.0 ml |

Method:

The antibiotic and active substance are dissolved or suspended in a mixture of the two excipients, with heating, and the resulting mixture is transferred, under aseptic conditions, into 5 ml ampules which have been cleaned and sterilized.

Example 4

Oily suspension containing 9-deoxy-11-deoxy-9,11-{imino-[2-(2-methoxyethoxy)-ethylidene]-oxy}-(9F)-erythromycin and N-(3,5-dibromo-2-hydroxy-benzyl)-trans-4-hydroxycyclohexylamine hydrochloride Composition:

| Antibiotic | 2500.0 mg |
| --- | --- |

-continued

| Active substance | 500.0 mg |
|---|---|
| Benzyl alcohol | 250.0 mg |
| Neutral oil q.s. ad | 25.0 ml |

Method:

The antibiotic and the active substance are dissolved or suspended in a mixture of the two excipients, with heating, and the resulting mixture is transferred, under aseptic conditions, into 25 ml injection vials which have been cleaned and sterilized.

Example 5

Two compartment preparation containing 9-deoxy-11-deoxy-9,11-{imino-[2-(2-methoxyethoxy)-ethylidene]-oxy}-(9F)-erythromycin lactobionate and N-(3,5-dibromo-2-hydroxy-benzyl)-trans-4-hydroxy-cyclohexylamine hydrochloride (aqueous suspension)

Composition:

| (a) Dry ampule. | |
|---|---|
| Antibiotic | 715.0 mg |
| (b) Ampule containing suspension/solution. | |
| Active substance | 100.0 mg |
| Polyethyleneglycol stearate | 1.0 mg |
| Sorbitol | 250.0 mg |
| Methyl hydroxyethyl cellulose | 15.0 mg |
| Water for injection q.s. ad | 5.0 ml |

Method:

To prepare the dry ampule the active substance is dissolved in water for injection, sterilized, freed from pyrogens by means of a suitable filter system, possibly by use of pyrogen adsorption layers, and then transferred under aseptic conditions, in the desired dosages, into 10 ml injection vials which have been cleaned and sterilized. These vials are freeze-dried in the usual way.

Next, to prepare the ampules of suspension/solution, the excipients are dissolved in water for injection purposes, and the solution is filtered to sterilize it and to remove any pyrogens. The active substance is suspended in this solution under aseptic conditions, and the suspension is transferred, with stirring, into 5 ml ampules which have been cleaned and sterilized.

Example 6

Two-compartment preparation containing 9-deoxy-11-deoxy-9,11-{imino-[2-(2-methoxyethoxy)-ethylidene]-oxy}-(9F)-erythromycin lactobionate and N-(3,5-dibromo-2-hydroxy-benzyl)-trans-4-hydroxy-cyclohexylamine hydrochloride (aqueous suspension)

Composition:

| (a) Dry ampule. | |
|---|---|
| Antibiotic | 3575.0 mg |
| (b) Ampule containing suspension/solution. | |
| Active substance | 500.0 mg |
| Polyethyleneglycol stearate | 5.0 mg |
| Sorbitol | 1250.0 mg |
| Methyl hydroxyethyl cellulose | 75.0 mg |
| Water for injection q.s. ad | 25.0 ml |

Method:

The ampules (a) and (b) are prepared by a procedure analogous to that of Example 5. However, the substances are transferred into 25 ml and 30 ml injection vials, respectively.

Example 7

Injectable solution containing oxytetracycline hydrochloride and N-(3,5-dibromo-2-hydroxy-benzyl)-trans-4-hydroxy-cyclohexylamine Composition:

| Antibiotic (× HCl) | 5.0 gm |
|---|---|
| Active substance | 0.05–0.8 gm |
| Magnesium oxide | 0.45 gm |
| pH Adjuster | 1.0 gm |
| Antioxidants | 0.2 gm |
| Solketal | 15.0 gm |
| 1,2-Propyleneglycol | 74.0 gm |
| Water for injection q.s. ad | 100.0 ml |

Method:

In a suitable vessel, the antibiotic is dissolved in the corresponding quantity of water, and 1,2-propyleneglycol and then magnesium oxide are added. At the same time, a solution of solketal and active substance in the corresponding quantity of 1,2-propyleneglycol is prepared. The two solutions of active substance are combined, and a solution of the antioxidants in a small amount of water is added thereto. The desired pH value is obtained by adding the pH adjuster. The solution is prepared and transferred into vials under a nitrogen atmosphere and under aseptic conditions. The solution must sterilized by filtration.

Example 8

Aqueous suspension containing chloramphenicol or thiamphenicol and N-(3,5-dibromo-2-hydroxy-benzyl)-trans-4-hydroxy-cyclohexylamine hydrochloride Composition:

| Antibiotic | 20.0 gm |
|---|---|
| Active substance | 0.05–2.5 gm |
| Suspension stabilizers | 1.6 gm |
| Emulsifier | 2.0 gm |
| Citric acid | 1.0 gm |
| Antifoaming agent | 0.2 gm |
| Thimerosal | 0.005 gm |
| 1 N Sodium hydroxide solution | 3.25 gm |
| Water for injection q.s. ad | 100.00 ml |

Method:

Thimerosal and citric acid are dissolved in about one-third of the quantity of water and placed in a suitable vessel. The active substance, suspension stabilizers, and antifoaming agent are successively added to this solution and dissolved or suspended therein.

The emulsifier is dissolved in about one-third of the quantity of water, with heating, and added thereto. A suspension of chloramphenicol in water is added, with stirring, while the homogeneous suspension is adjusted to the desired pH value with 1N NaOH, having been made up to 100 ml with the remaining water. All the excipients and active substances or solutions thereof are sterilized before use. The preparation must be made up and bottled under aseptic conditions.

Example 9

Injection solution containing tylosin and N-(2-amino-3,5-dibromobenzyl)-N-methyl-cyclohexylamine hydrochloride Composition:

| Tylosin | 50.0 mg |
|---|---|
| Active substance | 0.5–6.0 mg |
| 1,2-Propyleneglycol | 0.5 ml |
| Benzyl alcohol | 0.04 ml |
| Hydrochloric acid q.s. ad | pH 4 |
| Water for injection q.s. ad | 1.0 ml |

Method:
The active substance is dissolved in 90 ml of a suitable mixture of 1,2-propyleneglycol and water, with stirring and ultrasonic treatment, under a current of $N_2$. Tylosin is added and dissolved to form a clear solution. After the addition of the benzyl alcohol, the mixture is adjusted to the desired pH with 1N HCl and then made up to 100 ml with water. The solution must be prepared and bottled under aseptic conditions.

Example 10

Injection solution containing tylosin and N-(3,5-dibromo-2-hydroxy-benzyl)-trans-4-hydroxy-cyclohexylamine hydrochloride Composition:

| Tylosin | 50.0 mg |
|---|---|
| Active substance | 0.5–6.0 mg |
| 1,2-Propyleneglycol | 0.5 ml |
| Benzyl alcohol | 0.04 ml |
| Hydrochloric acid q.s. ad | pH 4 |
| Water for injection q.s. ad | 1.0 ml |

Method:
The above solution was prepared using a procedure analogous to that of Example 9.

Example 11

Oil suspension containing erythromycin and N-(3,5-dibromo-2-hydroxy-benzyl)-trans-4-hydroxy-cyclohexylamine hydrochloride Composition:

| Erythromycin | 50.0 mg |
|---|---|
| Active substance | 0.5–25.0 mg |
| Sodium dioctylsulfosuccinate | 2.0 mg |
| Neutral oil q.s. ad | 1.0 ml |

Method:
Sodium dioctylsulfosuccinate is dissolved in the corresponding quantity of neutral oil with heating and stirring. After the solution has cooled to ambient temperature, erythromycin is dissolved therein, and active substance of a suitable particle size is added. The resulting suspension is homogenized with a suitable stirrer and bottled under aseptic conditions.

Example 12

Suspension containing erythromycin and N-(2-amino-3,5-dibromobenzyl)-N-methyl-cyclohexylamine Composition:

| Erythromycin | 50.0 mg |
|---|---|
| Active substance | 0.5–25.0 mg |
| Neutral oil q.s. ad | 1.0 ml |

Method:
The above suspension was prepared using a procedure analogous to that of Example 11.

Example 13

Injection solution containing trimethoprim, sulfadimidine, sulfathiazole, and N-(2-amino-3,5-dibromo-benzyl)-N-methyl-cyclohexylamine hydrochloride Composition:

| Trimethoprim | 40.0 mg |
|---|---|
| Sulfadimidine | 100.0 mg |
| Sulfathiazole | 100.0 mg |
| Active substance | 0.5–6.0 mg |
| Glycerin formal q.s. ad | 1.0 ml |

Method:
The active substance is dissolved in glycerin formal with stirring, under a current of $N_2$. Then, trimethoprim, sulfadimidine, and sulfathiazole are successively dissolved therein, with stirring. The solution is then topped up with the remaining glycerin formal. The preparation must be made up and bottled under aseptic conditions and in the absence of direct light.

Example 14

Injection solution containing trimethoprim, sulfadimidine, sulfathiazole, and N-(3,5-dibromo-2-hydroxy-benzyl)-trans-4-hydroxy-cyclohexylamine hydrochloride Composition:

| Trimethoprim | 40.0 mg |
|---|---|
| Sulfadimidine | 100.0 mg |
| Sulfathiazole | 100.0 mg |
| Active substance | 0.5–15.0 mg |
| Glycerin formal q.s. ad | 1.0 ml |

Method:
The above solution was prepared using a procedure analogous to that of Example 13.

Example 15

Injection solution containing spiramycin and N-(2-amino-3,5-dibromo-benzyl)-trans-4-hydroxy-cyclohexylamine hydrochloride Composition:

| Active substance | 0.5–6.0 mg |
|---|---|
| Spiramycin | 50.0 mg |
| 1,2-Propyleneglycol | 0.5 ml |
| Water for injection q.s. ad | 1.0 ml |
| 1 N Hydrochloric acid q.s. ad | pH 3.8 |

Method:
The active substance is dissolved, with stirring, in a mixture of 1,2-propyleneglycol and water, under a current of $N_2$. Then, the spiramycin is dissolved therein. The solution is adjusted to the desired pH with 1N HCl and topped with water. The preparation should be made up and bottled under aseptic conditions.

Example 16

Injection solution containing spiramycin and N-(3,5-dibromo-2-hydroxy-benzyl)-trans-4-hydroxy-cyclohexylamine Composition:

| | |
|---|---|
| Active substance | 0.5–15.0 mg |
| Spiramycin | 50.0 mg |
| Glycofurol q.s. ad | 1.0 ml |

Method:

A solution of spiramycin in glycofurol is prepared under a current of $N_2$, and then the active substance is added in small amounts, again under a current of $N_2$, and dissolved therein. The solution is bottled under aseptic conditions and under $N_2$.

Example 17

Two-compartment preparation containing 9-deoxy-11-deoxy-9,11-{imino-[2-(2-methoxyethoxy)-ethylidene]-oxy}-(9F)-erythromycin lactobionate and N-(2-amino-3,5-dibromo-benzyl)-trans-4-hydroxy-cyclohexylamine hydrochloride Composition:

| | |
|---|---|
| (a) Dry ampule. | |
| Antibiotic | 715.0 mg |
| (b) Solution ampule. | |
| Active substance | 75.0 mg |
| Tartaric acid | 37.5 mg |
| Glycerin polyethyleneglycol oxystearate | 250.0 mg |
| Glucose | 200.0 mg |
| Water for injection q.s. ad | 5.0 ml |

Method:

The ampules (a) and (b) are prepared by a procedure analogous to that of Example 1.

The invention herein is not limited merely to the embodiments of the invention set forth in Examples 1 to 17. It is clear that the invention also encompasses incorporating other antibacterial substances or combinations of limited resorbability which are commonly used in veterinary medicine but have not been specifically mentioned above into the usual forms for administration together with a benzylamine derivative of Formula I.

The preceding specific embodiments are illustrative of the practice of the invention. It is to be understood, however, that other expedients known to those skilled in the art or disclosed herein, may be employed without departing from the spirit of the invention or the scope of the appended claims.

We claim:

1. A method of increasing the resorption of tylosin in an animal host, which comprises parenterally administering to said host (a) N-(2-amino-3,5-dibromo-benzyl)-N-methyl-cyclohexlamine in combination with (b) an effective antibacterial amount of tylosin, the weight ratio of component (a) to component (b) being from about 2:100 to 12:100.

2. An antibacterial pharmaceutical composition for parenteral administration into the tissue of an animal host in need of such administration which comprises (a) N-(2-amino-3,5-dibromo-benzyl)-N-methyl-cyclohexylamine and (b) an effective antibacterial amount of tylosin, the weight ratio of component (a) to component (b) being from about 2:100 to 12:100.

3. A method of increasing the resorption of tylosin in an animal host, which comprises parenterally administering to said host (a) N-(3,5-dibromo-2-hydroxy-benzyl)-trans-4-hydroxy-cyclohexylamine in combination with (b) an effective antibacterial amount of tylosin, the weight ratio of component (a) to component (b) being from about 4:100 to 12:100.

4. An antibacterial pharmaceutical composition for parenteral administration into the tissue of an animal host in need of such administration which comprises (a) N-(3,5-dibromo-2-hydroxy-benzyl)-trans-4-hydroxy-cyclohexylamine and (b) an effective antibacterial amount of tylosin, the weight ratio of component (a) to component (b) being from about 4:100 to 12:100.

* * * * *